United States Patent
Kimura et al.

(12) 
(10) Patent No.: US 6,338,956 B1
(45) Date of Patent: *Jan. 15, 2002

(54) STRESS-RESISTANT MICROORGANISM AND METHOD OF PRODUCING FERMENTATIVE PRODUCT

(75) Inventors: Eiichiro Kimura; Yoshimi Kikuchi; Yoshio Kawahara; Shinya Goto; Osamu Kurahashi; Tsuyoshi Nakamatsu, all of Kawasaki (JP)

(73) Assignee: Ajinomoto Co., Inc., Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 09/634,632

(22) Filed: Aug. 8, 2000

Related U.S. Application Data

(62) Division of application No. 08/894,223, filed as application No. PCT/JP96/00287 on Feb. 9, 1996, now Pat. No. 6,156,532.

(30) Foreign Application Priority Data

Feb. 20, 1995 (JP) ................................. 7-30458
Dec. 28, 1995 (JP) ............................... 7-343376

(51) Int. Cl.$^7$ ............................................... C12P 13/04
(52) U.S. Cl. ..................... 435/106; 435/108; 435/110; 435/115; 435/128; 435/132; 435/170; 435/171
(58) Field of Search ................................. 435/106, 110, 435/115, 108, 128, 132, 170, 171

(56) References Cited

PUBLICATIONS

Tilly et al. "The DNAK Protein Modulates the Heat–shock Response of *Escherichia Coli*", Cell, vol. 34, 641–646, Sep. 1983.

Hockney, "Recent Developments in Heterologous Protein Production in *Escherichia Coli*", Tibtech, vol. 12, pp. 456–463, Nov. 1994.

Meury et al, "Impairment of Nucleoid Segregation and Cell Division at High Osmolarity in Strain of *Escherichia Coli* Overproducing the Chaperone DNAK", Fems Microbiology Letters, vol. 113, 93–100, 1993.

Chemical Abstracts, vol. 116, No. 9, p. 486, Mar. 2, 1992, AN 80359A.

Kogoma et al, "Sensitization of *Escherichia Coli* Cells to Oxidative Stress by Deletion of the rpoH Gene, which Encodes the Heat Shock Sigma Factor", Journal of Bacteriology, vol. 174, No. 2, pp. 630–632, Jan. 1992.

Makrides et al, in Microbiological Review, 1996, vol. 60, No. 3, pp. 512–538.

Goloubinoff et al, "GroHeat–Shock Proteins Promote Assembly of Foreign Pkokaryoticribulose Bisphosphate Carboxylase Oligomers in *Escherichia Coli*", Nature, 337(6202): 44–47, Jan. 5, 1989.

Van Dyk et al, "Demonstration by Genetic Suppression of Interaction of GroE Products with Many Proteins", Nature, 342(6248): 451–453, Nov. 23, 1989.

Grossman et al, "The htpR Gene Product of *E. Coli* is a Sigma Factor for Heat–Shock Promoters", Cell., 38(2): 383–390, Sep. 1984.

Berry–Lowe et al, "Purification of Characterization of Glumate 1–Semialdehydeaminotransferase from Barley expressed in *E. Coli* ", Plant Physiol., 99: 1597–1603, 1992.

*Primary Examiner*—Ponnathapur Achutamurthy
*Assistant Examiner*—Kat Kerr
(74) *Attorney, Agent, or Firm*—Oblon, Spivak, McClelland, Maier & Neustadt, P.C.

(57) ABSTRACT

A microorganism is utilized to fermentatively produce useful substances such as amino acids by cultivating the microorganism in a medium to allow a fermentative product to be produced and accumulated in the medium, and collecting the fermentative product, wherein the microorganism to be used is modified by introduction of at least one of a gene coding for a heat shock protein and a gene coding for a σ factor which specifically functions for the heat shock protein gene to enhance expression amount of the heat shock protein in cells, whereby the microorganism is allowed to have added resistance to stress which would otherwise restrain growth of the microorganism and/or production of the fermentative product.

3 Claims, No Drawings

SEQUENCE LISTING

<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 1
cggaacgaag tttgatatca                                                    20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 2
atccagggtt ctctgcttaa                                                    20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 3
gacgtcgata gcaggccaat                                                    20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 4
gacgcactcg cgtcgtccgt                                                    20

STRESS-RESISTANT MICROORGANISM AND METHOD OF PRODUCING FERMENTATIVE PRODUCT

This application is a division of application Ser. No. 08/894,223, filed on Aug. 25, 1997, now U.S. Pat. No. 6,156,532, which was originally filed as International Application Number PCT/JP96/00287 on Feb. 9, 1996.

TECHNICAL FIELD

The present invention relates to a method of producing a fermentative product. In particular, the present invention relates to a method of fermentatively producing useful substances such as amino acids by utilizing microorganisms, and to microorganisms having added resistance to stress which would otherwise restrain growth of the microorganisms and/or production of the fermentative products.

BACKGROUND ART

When cells are exposed to stress such as high temperature, high osmotic pressure, metabolic inhibition, presence of heavy metal, and viral infection, a family of proteins called "heat shock proteins" (hereinafter referred to as "HSP") are induced and synthesized in a short period of time to cause a defense reaction against the stress. HSP presents broad homology ranging from procaryotic cells to eucaryotic cells, and it is roughly divided into several groups (HSP 60 group, HSP 70 group, HSP 90 group, TRiC group, and miscellaneous group) (Hendrick, J. P. and Hartl, F. V., *Annu. Rev. Biochem.*, 62, 349–384 (1993)).

The mechanism of stress resistance exhibited by HSP resides in the function of HSP to form higher-order structures of proteins (folding of proteins). Namely, when a protein is denatured due to stress, and becomes incapable of forming a correct higher-order structure, HSP binds to the protein, and the protein is subjected to refolding into the correct higher-order structure. Thus the protein can be returned to have its normal function.

HSP, which functions for the formation of higher-order structures of proteins as described above, has been revealed to serve as a molecular chaperon not only for denatured proteins but also for cells in a normal state through the process of protein folding, assembly, membrane transport and so on. Accordingly, its importance is recognized and widely noticed (Ellis, R. J. et al., *Science*, 250, 954–959 (1990)). The term "chaperon" means a supporter. This designation results from the fact that HSP binds to various proteins, and it exhibits its function.

Expression of HSP is induced when cells are exposed to stress as described above. The induction is usually temporary. It attenuates soon, and a new steady state is achieved. It has been revealed that the induction of HSP is made at the transcription level (Cowing, D. C. et al., *Proc. Natl. Acad. Sci. USA*, 80, 2679–2683 (198); Zhou, Y. N. et al., *J. Bacteriol.*, 170, 3640–3049 (1988)). It is known that each of the family of HSP genes has a promoter structure called "heat shock promoter", and sigma-32 ($\sigma^{32}$) is present which is a σ (sigma) factor to specifically function for the heat shock promoter. It is known that $\sigma^{32}$ is a protein encoded by a rpoH gene, having an extremely short half-life life of about 1 minute, and it closely relates to the temporary induction of HSP (Straus, D. B. et al., *Nature*, 329, 348–351 (1987)). It has been revealed that expression control for $\sigma^{32}$ itself is made at the transcription level and at the translation level, however, major control is made at the translation level.

The induction of HSP by heat shock is caused by two mechanisms of increase in synthetic amount of $\sigma^{32}$ and stabilization thereof. Among them, as for the increase in synthetic amount of $\sigma^{32}$, it has been already revealed that the structure of $\sigma^{32}$ changes due to heat, and thus translation is accelerated (Yura, T. et al., *Annu. Rev. Microbiol.*, 47, 321–350 (1993)). As for the stabilization of $\sigma^{32}$, it has been shown that HSP (DnaK or the like) participates in degradation of $\sigma^{32}$, assuming that feedback control by HSP functions (Tilly, K. et al., *Cell*, 34, 641–646 (1983); Liberek, K., *Proc. Natl. Acad. Sci. USA*, 89, 3516–3520 (1994)).

As for *Escherichia coli* (*E. coli*), it is known that the growth of cells relates to HSP in the presence of stress as described above (Meury, J. et al., *FEMS Microbiol. Lett.*, 113, 93–100 (1993)). It is also known that production of human growth hormone is affected by dnaK, and secretion of procollagenase is affected by aroE (Hockney, R. C., *Trends in Biotechnology*, 12, 456 (1994)). However, no relationship is known between HSP and productivity of fermentative products such as amino acids and nucleic acids and the like. As for coryneform bacteria, no relationship is known between HSP and growth, and no relationship is also known between HSP and productivity of fermentative products.

DISCLOSURE OF THE INVENTION

An object of the present invention is to clarify the relationships between HSP and growth of microorganisms and between HSP and productivity of fermentative products in order to decrease the influence of stress which restrains growth of microorganisms and/or production of fermentative products so that the productivity and the yield are improved instead of being lowered in production of useful substances such as amino acids by fermentation.

As a result of diligent investigations by the present inventors in order to achieve the object described above, it has been found out that the productivity and the growth can be improved by introducing, into a microorganism, a gene coding for HSP or a gene coding for a σ factor which specifically functions for the HSP gene, and enhancing expression of HSP. Thus the present invention has been completed.

Namely, the present invention lies in a method of producing a fermentative product by utilizing a microorganism, comprising the steps of cultivating the microorganism in a medium to allow the fermentative product to be produced and accumulated in the medium, and collecting the fermentative product, wherein the microorganism is modified by introduction of at least one of a gene coding for HSP and a gene coding for a σ factor which specifically functions for the HSP gene to enhance expression amount of HSP in cells, whereby the microorganism is allowed to have added resistance to stress which would otherwise restrain growth of the microorganism and/or production of the fermentative product.

In another aspect, the present invention lies in a microorganism for producing a fermentative product, wherein the microorganism is modified by introduction of at least one of a gene coding for HSP and a gene coding for a σ factor which specifically functions for the HSP gene to enhance expression amount of HSP in cells, whereby the microorganism is allowed to have added resistance to stress which would otherwise restrain growth of the microorganism and/or production of the fermentative product.

In a preferred embodiment, the method and the microorganism according to the present invention deal with various fermentative products including, for example, amino acids such as L-threoriine, L-lysine, L-glutamic acid, L-leucine, L-isoleucine, L-valine, and L-phenylalanine; nucleic acids or nucleosides such as guanylic acid, inosine, and inosinic acid; and other substances such as vitamins and antibiotics.

In another preferred embodiment, the stress includes temperature, osmotic pressure of the medium, and high concentration of the fermentative product which are not preferable for the growth of the microorganism.

In still another preferred embodiment, the gene coding for the heat shock protein specifically includes groE, and the gene coding for the σ factor specifically includes rpoH.

In still another preferred embodiment, the microorganism to which the present invention is applied includes bacteria belonging to the genus Escherichia, and coryneform bacteria.

The present invention will be described in detail below.

The fermentative product to which the present invention is applied is not specifically limited provided that it is those produced by fermentation by using any microorganism. The fermentative product includes those produced by microorganisms including, for example, various L-amino acids such as L-threonine, L-lysine, L-glutamic acid, L-leucine, L-isoleucine, L-valine, and L-phenylalanine; nucleic acids or nucleosides such as guanylic acid, inosine, and inosinic acid; and other substances such as vitamins and antibiotics. Even in the case of substances which are not produced at present by utilizing microorganisms, the present invention may be applied to those substances which will be capable of being produced by microorganisms, for example, as a result of success in genetic recombination. Among the substances described above, the method of the present invention may be preferably applied to those which are secreted to the medium to increase the osmotic pressure of the medium, especially such as amino acids.

There is no special limitation to the microorganism which is modified by introduction of at least one of the gene coding for HSP and the gene coding for the σ factor which specifically functions for the HSP gene to enhance expression amount of HSP in cells, thereby being allowed to have added resistance to stress that would otherwise restrain growth of the microorganism and/or production of the fermentative product, provided that the microorganism is those which produce any fermentative product by fermentation. The microorganism includes those which have been hitherto used for producing substances, including, for example, bacteria belonging to the genus Escherichia, coryneform bacteria, bacteria belonging to the genus Bacillus, and bacteria belonging to the genus Serratia. A preferable microorganism is such one in which a DNA fragment containing a replication origin of a plasmid is obtained, the HSP gene or the gene coding for the σ factor specific for the HSP gene operates, and the number of copies of these genes can be increased in the microorganism. The coryneform bacteria described above are a group of microorganisms as defined in *Bergey's Manual of Determinative Bacteriology*, 8th ed., p. 599 (1974), which are aerobic and non-acid-fast Gram-positive rods having no spore-forming ability, including bacteria belonging to the genus Corynebacterium, bacteria belonging to the genus Brevibacterium having been hitherto classified into the genus Brevibacterium but united at present as bacteria belonging to the genus Corynebacterium, and bacteria belonging to the genus Brevibacterium closely related to bacteria belonging to the genus Corynebacterium.

Specifically, exemplary microorganisms for each of fermentative products are as follows. Those suited for L-threonine include, for example, *Escherichia coli* VKPM B-3996 (RIA 1867) (see U.S. Pat. No. 5,175,107), and *Corynebactrium acetoacidophilum* AJ12318 (FERM BP-1172) (see U.S. Pat. No. 5,188,949). Those suited for L-lysine include, for example, *Escherichia coli* AJ11442 (NRRL B-12185, FERM BP-1543) (see U.S. Pat. No. 4,346, 170), *Escherichia coli* W3110(tyrA) (this strain is obtainable from *Escherichia coli* W3110(tyrA)/pHATerm (FERM BP-3653) by removing a plasmid pHATerm, see WO 95/16042 International Publication Pamphlet), *Brevibacterium lactofermentum* AJ12435 (FERM BP-2294) (see U.S. Pat. No. 5,304,476), and *Brevibacterium lactofermentum* AJ3990 (ATCC 31269) (see U.S. Pat. No. 4,066,501). Those suited for L-glutamic acid include, for example, *Escherichia coli* AJ12624 (FERM BP-3853) (see French Patent Publication No. 2,680,178), *Brevibacterium lactofermentum* AJ12821 (FERM BP-4172) (see Japanese Patent Laid-open No. 5-26811, and French Patent Publication No. 2,701,489), *Brevibacterium lactofermentum*AJ12475 (FERM BP-2922) (see U.S. Pat. No. 5,272,067), and *Brevibacterium lactofermentum* AJ13029 (FERM BP-5189) (see JP 95/01586 International Publication Pamphlet). Those suited for L-leucine include, for example, *Escherichia coli* AJ11478 (FERM P-5274) (see Japanese Patent Publication No. 62-34397), and *Brevibacterium lactofermentum* AJ3718 (FERM P-2516) (see U.S. Pat. No. 3,970,519). Those suited for L-isoleucine include, for example, *Escherichia coli* KX141 (VKPM B-4781) (see European Patent Publication No. 519,113), and *Brevibacterium flavum* AJ12149 (FERM BP-759) (see U.S. Pat. No. 4,656,135). Those suited for L-valine include, for example, *Escherichia coli* VL1970 (VKPM B-4411) (see European Patent Publication No. 519,113), and *Brevibacterium lactofermentum* AJ12341 (FERM BP-1763) (see U.S. Pat. No. 5,188,948). Those suited for L-phenylalanine include, for example, *Escherichia coli* AJ12604 (FERM BP-3579) (see Japanese Patent Laid-open No. 5-236947 and European Patent Publication No. 488,424), and *Brevibacterium lactofermentum* AJ12637 (FERM BP-4160) (see French Patent Publication No. 2,686, 898).

The microorganism to be used for the method of the present invention includes the microorganisms as described above, falling under the definition that the microorganism is modified by introduction of at least one of the gene coding for HSP and the gene coding for the σ factor which specifically functions for the HSP gene to enhance expression amount of HSP in cells, whereby the microorganism is allowed to have added resistance to stress which would otherwise restrain growth of the microorganism and/or production of the fermentative product. The gene to be introduced into the microorganism may be any one of, or both of the gene coding for HSP and the gene coding for the σ factor which specifically functions for the HSP gene.

The phrase "to enhance expression amount of HSP" means the increase in amount of HSP production of a microorganism which originally produces HSP, and it additionally implies that a microorganism, which does not substantially express HSP in its original state, becomes to express HSP. Specifically, the enhancement of expression amount of HSP is realized, for example, by introducing a foreign or endogenous HSP gene into cells of a microorganism, and expressing it therein. In such a procedure, the number of copies of the HSP gene in a cell can be increased by using a vector autonomously replicable in the microbial cell, especially a plasmid of the multiple copy type as the vector. Alternatively, the expression of HSP can be also efficiently enhanced by using a promoter having good expression efficiency to increase the amount of expression per one unit of the HSP gene. Alternatively, HSP can be also enhanced by introducing, into microbial cells, a σ factor gene which specifically functions for an inherent promoter for the HSP gene.

The gene coding for HSP includes, for example, groE (gene for GroELS), dnaK (gene for DnaK), and dnaJ (gene for DnaJ). Among them, groE is preferred. The σ factor, which specifically functions for these genes, is exemplified by rpoH which codes for $\sigma^{32}$. Microorganisms originating these genes are not specifically limited, provided that each of the genes is able to function in a cell of microorganism belonging to the genus Escherichia or coryneform bacteria, and concretely exemplifed by microorganisms belonging to the genus Escherichia and coryneform bacteria.

The rpoH gene and the groE gene of *Escherichia coli* have been already reported for their nucleotide sequences (rpoH: *J. Bacteriol.*, 170, 3479–3484 (1988); groE: *Nature*, 333, 330–334 (1988)). These genes can be obtained from *Escherichia coli* chromosome by means of amplification in accordance with a PCR (polymerase chain reaction) method by using oligonucleotide primers synthesized on the basis of the sequences. Nucleotide sequences of primers for amplifying the rpoH gene are exemplified by sequences shown in SEQ ID NOS: 1 and 2. Nucleotide sequences of primers for amplifying the groE gene are exemplified by sequences shown in SEQ ID NOS: 3 and 4.

It has been reported that the dnaK gene and the groE gene of *Brevibacterium flavum* are isolated by a PCR method utilizing primers prepared on the basis of the amino acid sequence conserved among the dnaK genes or the groE genes derived from *Escherichia coli* and *Bacillus subtilis*, and these genes are highly homologous to the dnaK genes or groE genes derived from other microorganisms (Abstracts of Lectures in the 1994 Meeting of the Molecular Biology Society of Japan, p. 395). Judging from the fact, it is expected that genes coding for the other HSP (dnaJ gene, rpoH gene and the like) also have high homology with each of the genes originating from *Escherichia coli*. Therefore, it is thought to be easy to isolate these genes from coryneform bacteria by means of hybridization method using the genes coding for HSP originating from *Escherichia coli*, or PCR method utilizing a part of the sequence of theses genes.

In order to introduce the gene obtained as described above into a bacterium belonging to the genus Escherichia, for example, a DNA fragment containing the gene may be ligated with vector DNA autonomously replicable in cells of bacteria belonging to the genus Escherichia, and an obtained recombinant vector may be used to transform the bacterium belonging to the genus Escherichia. In order to introduce the gene described above into a microorganism other than bacteria belonging to the genus Escherichia, a DNA fragment containing the gene may be ligated with vector DNA autonomously replicable in cells of the microorganism, and an obtained recombinant vector may be used to transform the microorganism.

Plasmid vector DNA is preferred as the vector DNA which can be used in the present invention. Those suited for bacteria belonging to the genus Escherichia as the microorganism into which the gene is introduced include, for example, pUC19, pUC18, pBR322, pHSG299, pHSG399, and RSF1010. Alternatively, vectors of phage DNA can be also utilized. In order to efficiently achieve expression of HSP, it is available to use promoters which operate in microorganisms, such as lac, trp, and PL instead of the inherent promoter for the HSP gene. In order to introduce, into the microorganism, the HSP gene or the σ factor which specifically functions for the HSP gene, DNA containing such a gene may be incorporated into chromosome of the microorganism in accordance with a method by using transposon (Berg, D. E. and Berg, C. M., *Bio/Technol.*, 1, 417 (1983)), Mu phage (Japanese Patent Laid-open No. 2-109985), or homologous recombination (*Experiments in Molecular Genetics*, Cold Spring Harbor Lab. (1972)).

The vector DNA which can be used in the present invention includes plasmid vectors autonomously replicable in coryneform bacteria, including, for example, pAM 330 (see Japanese Patent Publication No. 1-11280), and pHM1519 (see Japanese Patent Laid-open No. 58-77895) when the microorganism into which the gene is introduced is a coryneform bacterium.

The method for transformation is not especially different from ordinary ones for preparing transformants of microorganisms. For example, in the case of bacteria belonging to the genus Escherichia, transformation can be performed in accordance with a method of D. M. Morrison (*Methods in Enzymology*, 68, 326 (1979)), a method for treating recipient cells with calcium chloride to increase permeability for DNA (Mandel, M. and Higa, A., *J. Mol. Biol.*, 53, 159 (1970)) or the like. Coryneform bacteria can be transformed in accordance with the method of Mandel et al. described above, or a method for introduction during a proliferating phase (to provide so-called competent cells) so that the cells can incorporate DNA as reported for *Bacillus subtilis* (Duncan, C. H., Wilson, G. A. and Young, F. E., *Gene*, 1, 153 (1977)). Alternatively, recombinant DNA can be also introduced after converting DNA recipient cells into protoplasts or spheroplasts which easily incorporate recombinant DNA as known for *Bacillus subtilis*, Actinomycetes, and yeast (Chang, S. and Choen, S. N., *Molec. Gen. Genet.*, 168, 111 (1979); Bibb, M. J., Ward, J. M. and Hopwood, O. A., *Nature*, 274, 398 (1978); Hinnen, A., Hicks, J. B. and Fink, G. R., *Proc. Natl. Acad Sci. USA*, 75, 1929 (1978)). Alternatively, recombinant DNA can be also introduced into bacteria belonging to the genus Brevibacterium or Corynebacterium in accordance with an electric pulse method (Sugimoto et al., Japanese Patent Laid-open No. 2-207791).

Ordinary microorganisms undergo restraint of growth and decrease in productivity and yield of fermentative products when they suffer stress due to increase in cultivation temperature, high osmotic pressure caused by fermentative products or high concentration medium components, or metabolic abnormality associated with production of aimed fermentative products. On the contrary, it is possible to add resistance to such stress by enhancing expression of HSP. As a result, it is possible to increase the productivity of fermentative products in environments in which microorganisms suffer stress as described above. The resistance to stress does not mean complete resistance, and hence it also includes properties to decrease influences caused by the stress. Both of the restraint of growth and the decrease in productivity and yield of fermentative products are not necessarily desensitized depending on the type of genes to be introduced and the type of host microorganisms. There is sometimes a case in which the yield of a fermentative product is improved although the growth is restrained. The stress, against which the resistance can be added in accordance with the method of the present invention, includes, for example, temperature, osmotic pressure of a medium, and high concentration amino acid in a medium which are not preferable for the growth of the microorganism.

The medium for production by fermentation to be used for the method of the present invention may be well-known media having been hitherto used depending on microorganisms to be utilized. Namely, it is an ordinary medium containing a carbon source, a nitrogen source, inorganic ions, and optionally other organic components. No special medium is required to carry out the present invention.

Those which are usable as the carbon source include, for example, sugars such as glucose, lactose, galactose, fructose, and starch hydrolysate; alcohols such as glycerol and sorbitol; and organic acids such as fumaric acid, citric acid, and succinic acid.

Those which are usable as the nitrogen source include, for example, inorganic ammonium salts such as ammonium sulfate, ammonium chloride, and ammonium phosphate; organic nitrogen such as soybean hydrolysate; ammonia gas; and aqueous ammonia.

It is desirable to contain, as organic trace nutrient sources, required substances such as vitamin $B_1$, L-homoserine, and L-tyrosine; yeast extract or the like in appropriate amounts. Besides them, potassium phosphate, magnesium sulfate, iron ion, manganese ion and so on are added in small amounts, if necessary.

Cultivation may be performed under well-known conditions having been hitherto used depending on microorganisms to be utilized. Cultivation is preferably performed, for example, under an aerobic condition for 16 to 120 hours. The cultivation temperature is controlled at 25° C. to 45° C., and pH is controlled at 5 to 8 during the cultivation. For pH adjustment, it is possible to use inorganic or organic, acidic or alkaline substances, ammonia gas and so on.

In the present invention, the metabolic product is collected from a medium liquid after completion of the cultivation with no necessity for any special method. Namely, the present invention can be carried out by combining methods of ion exchange resin, precipitation and others having been hitherto well-known.

BEST MODE FOR CARRYING OUT THE INVENTION

The present invention will be described in more detail below with reference to Examples.

EXAMPLE 1

Preparation of Plasmids for Introducing rpoH Gene and groE Gene

<1> Clonina of rpoH Gene and groE Gene

A rpoH gene and a groE gene of *Escherichia coli* were cloned in accordance with the PCR (polymerase chain reaction) method. Primers used in the PCR method were synthesized on the basis of sequences of the rpoH gene (*J. Bacteriol.*, 170, 3479–3484 (1988)) and the groE gene (*Nature*, 333, 330–334 (1988)) of *Escherichia coli* already reported. Oligonucleotides having nucleotide sequences shown in SEQ ID NO: 1 (5' side) and SEQ ID NO: 2 (3' side) were synthesized as primers for amplifying the rpoH gene. Oligonucleotides having nucleotide sequences shown in SEQ ID NO: 3 (5' side) and SEQ ID NO: 4 (3' side) were synthesized as primers for amplifying the groE gene.

(Primers for amplifying rpoH gene)

5' side: 5'-CGGAACGAAGTTTGATATCA-3' (SEQ ID NO: 1)

3' side: 5'-ATCCAGGGTTCTCTGCTTAA-3' (SEQ ID NO: 2)

(Primers for amplifying groE gene)

5' side: 5'-GACGTCGATAGCAGGCCAAT-3' (SEQ ID NO: 3)

3' side: 5'-GACGCACTCGCGTCGTCCGT-3' (SEQ ID NO: 4)

Chromosomal DNA was extracted from *E. coli* K-12 strain in accordance with a method of Saito et al. (Saito, H. and Miura, K., *Biochem. Biophys. Acta.*, 72, 619 (1963)), and it was used as a template to perform PCR by using the oligonucleotides described above as the primers.

The reaction was repeated over 25 cycles in PCR, each cycle comprising heat denaturation (94° C., 1 minute), annealing (37° C., 2 minutes), and polymerase reaction (72° C., 3 minutes).

Both ends of obtained amplified products were blunt-ended by using a commercially available DNA blunt end formation kit (produced by Takara Shuzo, Blunting kit). After that, the products were respectively cloned into a HincII site of a vector plasmid pSTV28 (produced by Takara Shuzo) to obtain plasmids pSTV28-rpoH and pSTV28-groE.

<2> Introduction of Replication Oriain from Coryneform Bacterium into Plasmid Containing rpoH Gene and Plasmid Containing groE Gene In order to make pSTV28-rpoH to be autonomously replicable in cells of coryneform bacteria, a replication origin (Japanese Patent Laid-open No. 5-007491) originating from an already obtained plasmid pHM1519 autonomously replicable in coryneform bacteria (Miwa, K. et al., *Agric. Biol. Chem.*, 48 (1984) 2901–2903) was introduced into pSTV28-rpoH. Specifically, pHM1519 was digested with restriction enzymes BamHI and KpnI to obtain a DNA fragment containing the replication origin. The obtained fragment was blunt-ended by using a DNA blunt end formation kit (produced by Takara Shuzo, Blunting kit), and then a KpnI linker (produced by Takara Shuzo) was ligated with its ends. The fragment was inserted into a KpnI site of pSTV28-rpoH to obtain pRPH. On the other hand, a plasmid pHSG399 having no rpoH gene was used as a control. The replication origin originating from pHM1519 was also inserted into a SalI site of the control plasmid by using a SalI linker (produced by Takara Shuzo) to obtain pSAC4.

EXAMPLE 2

Production of L-Glutamic Acid by L-Glutamic Acid-producina Bacterium with Introduced rpoH Gene pRPH and pSAC4 prepared as described above were introduced into *Brevibacterium lactofermentum* AJ12821 (FERM BP-4172) having L-glutamic acid-producing ability. L-Glutamic acid productivity of transformants containing each of the introduced plasmids was evaluated. The plasmids were introduced into cells of *Brevibacterium lactofermentum* by using an electric pulse method (Japanese Patent Laid-open No. 2-207791).

The transformants containing the introduced plasmids were selected on a CM2G plate medium (containing 10 g of polypeptone, 10 g of yeast extract, 5 g of glucose, 5 g of NaCl, and 15 g of agar in 1 L of pure water, pH 7.2) containing 4 μg/ml of chloramphenicol.

The L-glutamic acid productivity of the obtained transformants was evaluated as follows. Each of the transformants was cultivated on the CM2G plate medium to refresh cells. Each of the refreshed transformants was cultivated at 35° C. for 20 hours in a medium containing 80 g of glucose, 1 g of $KH_2PO_4$, 0.4 g of $MgSO_4.7H_2O$, 30 g of $(NH_4)_2SO_4$, 0.01 g of $FeSO_4.7H_2O$, 0.01 g of $MnSO_4.7H_2O$, 15 ml of soybean hydrolysate solution, 200 μg of thiamine hydrochloride, 300 μg of biotin, 4 mg of chloramphenicol, and 50 g of $CaCO_3$ in 1 L of pure water (at pH adjusted to 8.0 with KOH). Usually, *Brevibacterium lactofermentum* is preferably cultivated at a cultivation temperature of 31 to 32° C.

The bacterial cell concentration, and the amount of L-glutamic acid accumulated in the medium were measured after the cultivation. L-Glutamic acid was quantitatively determined by using Biotec Analyzer AS-210 produced by Asahi Chemical Industry. The bacterial cell concentration was determined by measuring the absorbance at 660 nm ($OD_{660}$) of the culture liquid diluted 51 times with 0.2 N hydrochloric acid. Results are shown in Table 1.

TABLE 1

| Bacterial strain | L-Glutamic acid (g/dl) | OD |
| --- | --- | --- |
| AJ12821/pSAC4 | 3.3 | 0.98 |
| AJ12821/pRPH | 4.3 | 0.68 |

As clarified from the results, although the growth was restrained, the L-glutamic acid productivity was improved in the L-glutamic acid-producing bacterium of *Brevibacterium lactofermentum* containing the introduced rpoH gene.

EXAMPLE 3

Production of L-Lysine by L-Lysine-producina Bacterium with Introduced rpoH Gene pRPH and pSAC4 prepared as described above were introduced into *Brevibacterium lactofermentum* AJ12435 (FERM BP-2294) exhibiting resistance to S-(2-aminoethyl)-L-cysteine and having L-lysine-producing ability derived by mutation from *Brevibacterium lactofermentum* ATCC 13869. L-Lysine productivity of transformants harboring each of the introduced plasmids was evaluated.

The plasmids were introduced into cells of *Brevibacterium lactofermentum* by using an electric pulse method (Japanese Patent Laid-open No. 2-207791).

The transformants harboring the plasmids were selected on a CM2G plate medium (containing 10 g of polypeptone, 10 g of yeast extract, 5 g of glucose, 5 g of NaCl, and 15 g of agar in 1 L of pure water, pH 7.2) containing 4 µg/ml of chloramphenicoi.

The L-lysine productivity of the obtained transformants was evaluated as follows. Each of the transformants was cultivated on the CM2G plate medium to refresh cells. Each of the refreshed transformants was cultivated at 31.5° C. for 60 hours in a medium containing 100 g of glucose, 1 g of $KH_2PO_4$, 0.4 g of $MgSO_4 \cdot 7H_2O$, 30 g of $(NH_4)_2SO_4$, 0.01 g of $FeSO_4 \cdot 7H_2O$, 0.01 g of $MnSO_4 \cdot 7H_2O$, 15 ml of soybean hydrolysate solution, 200 µg of thiamine hydrochloride, 300 µg of biotin, 4 mg of chloramphenicol, and 50 g of $CaCO_3$ in 1 L of pure water (at pH adjusted to 8.0 with KOH). The bacterial cell concentration, and the amount of L-lysine accumulated in the medium were measured after the cultivation. L-Lysine was quantitatively determined as L-lysine hydrochloride by using Biotec Analyzer AS-210 produced by Asahi Chemical Industry. The bacterial cell concentration was determined by measuring the absorbance at 660 nm ($OD_{660}$) of the culture liquid diluted 51 times with 0.2 N hydrochloric acid. Results are shown in Table 2.

TABLE 2

| Bacterial strain | L-Lysine hydrochloride (g/L) | OD |
| --- | --- | --- |
| AJ11446/pSAC4 | 22 | 0.78 |
| AJ11446/pRPH | 27 | 1.15 |

As shown in Table 2, the growth was good, and the L-lysine productivity was also improved in the L-lysine-producing bacterium of *Brevibacterium lactofermentum* containing the introduced rpoH gene. It is supposed that this result arose from mitigation of the influence of increased osmotic pressure due to accumulation of L-lysine.

EXAMPLE 4

Production of L-Phenylalanine by L-Phenylalanine-producina *Escherichia coli* with Introduced groE Gene pSTV28-groE or pSTV28 prepared as described above was introduced into a phenylalanine-producing bacterium, AJ12604 strain (FERM BP-3579) bred from *Escherichia coli* K-12 strain. L-Phenylalanine productivity of transformants harboring each of the introduced plasmids was evaluated.

The plasmids were introduced by using an electric pulse method (Japanese Patent Laid-open No. 2-207791). The transformants harboring the plasmids were selected on an L plate medium (containing 10 g of polypeptone, 5 g of yeast extract, 5 g of NaCl, and 15 g of agar in 1 L of pure water, pH 7.2) containing 40 µg/ml of chloramphenicol.

The L-phenylalanine productivity of the obtained transformants was evaluated as follows. The transformants were cultivated on the L plate medium containing 40 mg/L of chloramphenicol to refresh cells. Each of the refreshed transformants was cultivated at 45° C. for 40 hours in a medium containing 20 g of glucose, 29.4 g of $Na_2HPO_4$, 6 g of $KH_2PO_4$, 1 g of NaCl, 2 g of $NH_4Cl$, 10 g of sodium citrate, 0.4 g of sodium glutamate, 3 g of $MgSO_4 \cdot 7H_2O$, 0.23 g of KCl, 2 mg of thiamine hydrochloride, 75 mg of L-tyrosine, and 40 mg of chloramphenicol in 1 L of pure water (at pH adjusted to 7.0 with KOH). The bacterial cell concentration, and the amount of L-phenylalanine accumulated in the medium were measured after the cultivation. L-Phenylalanine was quantitatively determined by using Biotec Analyzer AS-210 produced by Asahi Chemical Industry. The bacterial cell concentration was determined by measuring the absorbance at 660 nm ($OD_{660}$) of the culture liquid diluted 51 times with pure water. Results are shown in Table 3.

TABLE 3

| Bacterial strain | L-Phenylalanine (g/L) | OD |
| --- | --- | --- |
| AJ12604/pSTV28 | 1.5 | 0.143 |
| AJ12604/pSTV28-qroE | 2.0 | 0.146 |

According to the results, it is clear that the productivity of L-phenylalanine was improved in E. coli with the introduced groE gene.

EXAMPLE 5

Production of L-Lysine by L-Lysine-producing Escherichia coli with Introduced rpoH Gene Escherichia coli W3110 (tyrA) strain was used as a host for L-lysine production. W3110 (tyrA) strain is described in detail in European Patent Publication No. 488424 (1992). However, its preparation method will be briefly described as follows.

E. coli W3110 strain was obtained from National Institute of Genetics (Mishima-shi, Shizuoka-ken, Japan). This strain was spread over an LB plate containing streptomycin, and strains which formed colonies were selected to obtain a streptomycin-resistant strain. The selected streptomycin-resistant strain was mixed with E. coli K-12 ME8424 strain to induce conjugation by stationarily cultivating them for 15 minutes under conditions at 37° C. in a complete medium (L-Broth: 1% Bacto trypton, 0.5% , Yeast extract, 0.5% NaCl). E. coli K-12 ME8424 strain has inherited characters of (HfrP045, thi, relA1, tyrA::Tn10, ung-1, nadB), and it is obtainable from National Institute of Genetics. After the conjugation, the culture was spread over a complete medium (L-Broth: 1% Bacto trypton, 0.5% Yeast extract, 0.5% NaCl, 1.5% agar) containing streptomycin, tetracycline, and L-tyrosine to select a strain which formed colonies. This strain was designated as E. coli W3110 (tyrA).

Many strains, which were formed by introducing plasmids into this strain, are described in European Patent Publication No. 488424 (1992). For example, a strain, which was obtained by introducing a plasmid pHATerm, was designated as Escherichia coli W3110 (tyrA)/pHATerm, was deposited in National Institute of Bioscience and Human Technology of Agency of Industrial Science and Technology (1-3, Higashi 1-chome, tsukuba-shi, ibaraki-ken, 305 Japan) based on Budapest Treaty on Nov.16, 1991, as accession number of FERM BP-3653. Escherichia coli W3110 (tyrA) strain can be obtained by removing the plasmid pHATerm from this bacterial strain by using an ordinary method.

A plasmid RSFD80 having a gene for lysine biosynthesis was introduced into the Escherichia coli W3110 (tyrA) strain in accordance with the method described in Example 4. RSFD80 is described in WO 95/16042 International Publication Pamphlet, and it contains DNA coding for dihydrodipicolinate synthase with desensitized feedback inhibition by L-lysine, and DNA coding for aspartokinase with desensitized feedback inhibition by L-lysine. E. coli JM109 strain harboring the RSFD80 plasmid was designated as AJ12396, and was deposited in National Institute of Bioscience and Human Technology of Agency of Industrial Science and Technology (1–3, Higashi 1-chome, tsukuba-shi, ibaraki-ken, 305 Japan) on Oct. 28, 1993, as accession number of FERM P-13936, and transferred from the original deposition to international deposition based on Budapest Treaty on Nov. 1, 1994, and has been deposited as accession number of FERM BP-4859.

A transformant of the W3110 (tyrA) strain, in which RSFD80 was introduced, was selected on a plate medium containing 50 $\mu$g/ml of streptomycin.

On the other hand, a plasmid for introducing the rpoH gene was constructed as follows. The rpoH gene was amplified by the PCR method in accordance with the method described in the item <1> in Example 1. An obtained amplified product was blunt-ended at its both ends by using a commercially available DNA blunt end formation kit (produced by Takara Shuzo, Blunting kit), and then it was cloned into a HincII site of a vector plasmid pMW119 (produced by Wako Pure Chemical Industries) to obtain a plasmid pMWrpoH. This plasmid was introduced into Escherichia coli W3110 (tyrA)/RSFD80 strain in accordance with the method described above. A transformant containing the introduced plasmid was selected on an L plate medium containing 50 $\mu$g/ml of streptomycin and 50 $\mu$g/ml of ampicillin.

The L-lysine productivity was evaluated for Escherichia coli W3110 (tyrA)/RSFD80 strain, and Escherichia coli W3110 (tyrA)/RSFD80+pMWrpoH strain obtained as described above.

The L-lysine productivity of the obtained transformants was evaluated as follows. The transformants were cultivated on the L plate medium to refresh cells. Each of the refreshed transformants was cultivated at 37° C. for 30 hours in a medium containing 40 g of glucose, 1 g of $KH_2PO_4$, 0.01 g of $MnSO_4.7H_2O$, 0.01 g of $FeSO_4.7H_2O$, 2 g of yeast extract, 0.1 g of L-tyrosine, 1 g of $MgSO_4.7H_2O$, and 25 g of CaCO in 1 L of pure water (at pH adjusted to 7.0 with KOH). In this experiment, the transformants were also cultivated in the same medium except that 40 g/L of L-lysine hydrochloride was initially added. L-Lvsine was quantitatively determined by using Biotec Analyzer AS-210 produced by Asahi Chemical Industry. Table 4 shows amounts of increase in L-lysine (obtained by subtracting the amount of initially added L-lysine from the amount of L-lysine in the medium after the cultivation) as amounts of L-lysine hydrochloride.

TABLE 4

| Bacterial strain | Production amount of L-lysine hydrochloride (g/L) Initially added L-lysine hydrochloride (g/L) | |
|---|---|---|
| | 0 | 40 |
| W3110 (tyrA)/RSFD80 | 9.17 | 6.43 |
| W3110 (tyrA)/RSFD80 + pMWrpoH | 9.22 | 7.64 |

According to the results, it is clear that the L-lysine productivity was improved in Escherichia coli containing the introduced rpoH gene even in the presence of the high concentration of L-lysine as compared with the strain containing no introduced rpoH gene.

Industrial Applicability

The relationships between HSP and growth of microorganisms and between HSP and productivity of fermentative products have been clarified by the present invention. Thus it is possible to decrease the influence of stress and improve deterioration of productivity and yield in fermentative production of useful substances such as amino acids.

What is claimed is:

1. A method of producing an amino acid selected from the group consisting of glutamic acid, lysine and phenylalanine, comprising:
   culturing a prokaryotic microorganism having the ability to produce and accumulate the amino acid in the medium in which the microorganism is cultured, and collecting the amino acid, wherein:
      said microorganism is modified by introduction of at least one of either a gene coding for a heat shock protein or a gene coding for a σ factor which functions to enhance expression amounts of heat shock proteins in said microorganism.

2. The method according to claim 1, wherein said microorganism has resistance to a temperature, an osmotic pressure of the medium, or a high concentration of the amino acid which is not preferable for the growth of the microorganism.

3. The method according to claim 1, wherein said microorganism is a bacterium belonging to the genus Escherichia or a coryneform bacterium.

* * * * *